(12) United States Patent
Smith et al.

(10) Patent No.: US 8,287,337 B2
(45) Date of Patent: Oct. 16, 2012

(54) COLD STORAGE DOORWAY WITH AIRFLOW CONTROL SYSTEM AND METHOD

(75) Inventors: Peter Smith, Lewistown, MT (US);
Daniel J. Rhyner, Lewistown, MT (US);
Carl E. Steele, Lewistown, MT (US)

(73) Assignee: HCR Incorporated, Lewistown, MT (US)

( * ) Notice: Subject to any disclaimer, the term of this patent is extended or adjusted under 35 U.S.C. 154(b) by 1248 days.

(21) Appl. No.: 11/649,513

(22) Filed: Jan. 4, 2007

(65) Prior Publication Data
US 2008/0233859 A1    Sep. 25, 2008

(51) Int. Cl.
*F24F 9/00* (2006.01)

(52) U.S. Cl. .................................. 454/188; 454/189

(58) Field of Classification Search ............... 454/188, 454/189, 190, 191, 192, 193
See application file for complete search history.

(56) References Cited

U.S. PATENT DOCUMENTS

| | | | |
|---|---|---|---|
| 1,090,562 A | 3/1914 | Orr | |
| 1,172,561 A | 2/1916 | Rowntree | |
| 2,283,577 A | 5/1942 | Roby | |
| 2,497,370 A | 2/1950 | Phillips | |
| 2,532,756 A | 12/1950 | Carr | |
| 2,939,374 A | 6/1960 | Caille | |
| 3,190,207 A | 6/1965 | Weisz | |
| 3,215,058 A | 11/1965 | Haas | |
| 3,224,500 A | 12/1965 | Bennett | |
| 3,251,196 A * | 5/1966 | Watkins | 62/158 |
| 3,301,162 A | 1/1967 | Zumblel | |
| 3,326,012 A * | 6/1967 | Asker et al. | 62/78 |
| 3,327,935 A | 6/1967 | Berlant | |
| 3,332,334 A | 7/1967 | Melzer | |
| 3,350,994 A | 11/1967 | Guibert | |
| 3,525,483 A | 8/1970 | Van Alslyne | |
| 3,629,973 A | 12/1971 | Bond | |
| 4,233,938 A | 11/1980 | Ruetenik | |
| 4,516,482 A | 5/1985 | Smith | |
| 4,619,075 A | 10/1986 | Wiles | |
| 5,042,198 A | 8/1991 | Privratsky | |
| 5,187,945 A | 2/1993 | Dixon | |
| 6,079,483 A * | 6/2000 | Morooka et al. | 165/11.1 |
| 6,106,387 A * | 8/2000 | Smith | 454/190 |
| 6,442,957 B1 | 9/2002 | Voogt et al. | |
| 6,470,698 B2 | 10/2002 | Nishi et al. | |
| 8,505,075 | 1/2003 | Gast et al. | |
| 6,595,429 B1 * | 7/2003 | Carlson et al. | 236/44 R |
| 8,595,429 | 7/2003 | Carlson et el. | |
| 6,874,331 B2 | 4/2005 | Chandler et al. | |
| 6,960,129 B2 | 11/2005 | Ashley et al. | |
| 2004/0134128 A1 | 7/2004 | Berry | |
| 2004/0261318 A1 | 12/2004 | Berry | |
| 2005/0005524 A1 | 1/2005 | Berry | |

* cited by examiner

*Primary Examiner* — Steven B McAllister
*Assistant Examiner* — Brittany E Towns
(74) *Attorney, Agent, or Firm* — Holland & Hart LLP (57) ABSTRACT

A conditioned vestibule, control system, and method are disclosed for use with a cold storage doorway that separates warm and cold sides. A heater warms an air stream discharged across the doorway by the vestibule. A control unit operates the heater to maintain an air stream temperature. The control unit continuously monitors the air stream temperature and operates the heater to maintain the air stream temperature in a non-saturated state based on a humidity ratio. One embodiment calculates first and second temperatures based, respectively, warm and cold side tangent lines to a psychrometric saturation curve and based on the humidity ratio. The tangent lines are based on humidity and temperature sensed on the warm and cold sides. The air stream is warmed to at least the greater of the first and second temperatures. One embodiment controls air flow to adjust the humidity ratio to more efficiently operate the vestibule.

28 Claims, 10 Drawing Sheets

COLD STORAGE DOORWAY WITH AIRFLOW CONTROL SYSTEM AND METHOD

FIELD OF INVENTION

The present invention relates to a conditioned vestibule for a cold storage doorway. More particularly, the present invention relates to an air curtain arrangement and control system that controls temperature of the air discharged across a doorway and a method of controlling the airflow temperature.

BACKGROUND INFORMATION

In the field of large cold storage freezers and similar devices, various systems such as solid doors, strip curtains, and air curtains, may be used to separate the cold storage room from an adjacent relatively warm anteroom. It is desirable to allow traffic from people and equipment through a doorway between the cold storage room and the adjacent warm room safely and with a minimum transfer of cool air from the cold room to the warm room.

The use of air curtains is one method of allowing a doorway to remain open to traffic while also preventing substantial energy loss between the cold and warm sides of the vestibule. Air curtains generally direct air across the doorway to counter infiltration of warm to the cold room and exfiltration of cold air from the cold room. By way of example, air curtains may direct air horizontally across the doorway or vertically, from an upper portion of the air curtain.

As a safety precaution, it is desirable prevent the formation of fog, ice, and water in the doorway. Ice may form from the mixing of air from the cold and warm sides of the vestibule. The formation of ice at an air curtain depends on the temperature and relative humidity of the cold and warm rooms, and may be characterized by a psychrometric saturation curve. The mixing of air from the relatively warm and cold sides may be characterized by a straight line between points representing the warm side temperature and humidity and the cold side temperature and humidity, which may be plotted on a psychrometric saturation chart along with the curve. Generally, ice may form whenever the mixing line is to the left of, and above, the psychrometric saturation curve, as it is typically plotted.

The formation of ice may be prevented by heating the air discharged from the air curtain. By way of example, the discharged air may be heated to a temperature at a point on the psychrometric saturation chart such that lines to such point from both the cold side and warm side temperature/humidity points remain to the right of, and below, the psychrometric saturation curve, as it is typically plotted.

While avoiding the formation of ice, water, and fog, it is also desirable to operate the air curtain as efficiently as possible, by adding the minimum amount of heat necessary to avoid such problems. With respect to the psychrometric saturation chart, this means keeping the point representing the airstream with the added heat as close to the saturation curve as possible, without causing mixing lines from this point to the cold side and warm side temperature/humidity points to contact or cross the saturation curve.

Because temperature and humidity conditions in the cold and warm side rooms may change, it is desirable in some applications to dynamically condition the discharged air in response to changing conditions. Conventional systems have various shortcomings. Some systems permit operation of the air curtain at points directly on the saturation curve. In changing environments, this permits the formation of ice, water, and fog because the system may not respond as quickly as the conditions change and because the sensors may not be sufficiently accurate for all positions in the vestibule. This is particularly a problem for systems that rely upon mathematical approximations of the psychrometric saturation curve. Also, conventional control systems do not apply to multiple air curtain arrangements. A vestibule may be formed with two or more air curtains positioned adjacent each other across a doorway. Multiple air curtain arrangements—particularly those having three or more air curtains—present a more complex situation than do single air curtains. As a result, conventional systems for dynamically conditioning air do not operate efficiently, or even properly, in multiple air curtain arrangements.

SUMMARY OF THE INVENTION

There exists a need to provide an air curtain and method for dynamically conditioning air which overcomes at least some of the above-referenced deficiencies. Accordingly, at least this and other needs have been addressed by exemplary embodiments of the air curtain arrangement with control system and method according to the present invention. One such embodiment is directed to an air curtain arrangement for a cold storage doorway. The arrangement includes a discharge means that discharges an air stream across a doorway having a cold side and a warm side. A heater warms the air stream. A control unit operates the heater to maintain an air stream temperature. An air return means receives the air discharged across the opening. An air stream temperature sensor provides an air stream temperature input to the controller. The control unit continuously monitors the air stream temperature and operates the heater to maintain the air stream temperature in a non-saturated state based on a humidity ratio of mixed air in the air curtain.

In another exemplary embodiment of the present invention, an air curtain arrangement for a cold storage doorway is provided. The arrangement includes means for directing an air stream across the doorway and means for maintaining a temperature at the air stream based on a humidity ratio associated with the doorway.

In yet another exemplary embodiment of the present invention, a method of controlling airstream temperature of an air curtain used in connection with an air curtain arrangement for a cold storage doorway that separates relatively warm and cold sides. Warm and cold side temperatures are continuously monitored. An air stream temperature is continuously determined based upon the warm and cold side temperatures and a humidity ratio of the discharged air. The air stream temperature is sufficient to operate the vestibule in a non-saturated state. The air stream moves across the doorway, while the air stream is maintained at the determined air stream temperature.

In yet another exemplary embodiment of the present invention, a conditioned vestibule for a cold storage doorway is provided. The vestibule includes first and second air curtains positioned adjacent each other. The air curtains direct an air stream across a doorway that separates a relatively warm side and a relatively cold side. A control unit operates a heater to maintain the air stream of at least one of the air curtains at a temperature based on a humidity ratio of the air curtain.

In yet another exemplary embodiment of the present invention, a method of maintaining an air stream temperature of an air curtain in a vestibule at a doorway between a relatively cold side and a relatively warm side is provided. Temperatures of a relatively warm and a relatively cold side of a doorway comprising an air curtain that directs an air stream across the doorway are continuously monitored. The air stream is maintained at a temperature based on the temperature of the relatively warm side and the relatively cold side, and based on a humidity ratio of mixed air in the air curtain.

In another exemplary embodiment of the present invention, a control unit is provided for controlling temperature of an air stream directed across a doorway by one or more air curtains that are part of an air curtain arrangement separating relatively warm and cold air masses. The control unit includes a processor and a storage arrangement, such as memory. The storage arrangement stores computer-executable instructions for execution by the processor to control operation of the air curtain arrangement. The instructions include instructions for continuously monitoring an air characteristic of at least one the relatively warm and cold air masses. The instructions also include instructions for continuously monitoring an air stream temperature, and operating a heater to warm the air stream temperature based on the monitoring of the air characteristic. The instructions ensure that the air stream temperature is sufficiently high to enable the vestibule to operate in a non-saturated state, based upon a humidity ratio of mixed air in the one or more air curtains.

In yet another exemplary embodiment of the present invention, an apparatus is provided for forming an air stream across a doorway between areas of relatively cool and warm air masses including a supply air plenum with an outlet aperture at a first side of the doorway, a return air duct with an inlet aperture at a second side of the doorway and an intermediate air duct extending between the supply plenum and return air duct. The apparatus includes an air mover for moving an air stream across the doorway into the inlet aperture to the return air duct through the intermediate air duct to the supply air plenum and out of the outlet aperture. The apparatus further includes a heater in thermal communication with the air stream for warming the air stream, and a control unit controlling the operation of the heater. A first air sensor is located in one of the relatively cool and warm air areas providing an air characteristic input to the control unit. A second air sensor is located in contact with the air stream providing an air stream characteristic input to the control unit. The control unit continuously monitors the air characteristic input and the air stream characteristic input and operates the heater to maintain the temperature of the air stream at a point below a line representing the mixing of the air stream with one or both of the air masses that is tangent to the psychrometric saturation curve.

In yet another exemplary embodiment of the present invention, an apparatus is provided for forming at least two air streams across a doorway between areas of relatively cool and warm air masses using first and second air curtains. Each air curtain includes a supply air plenum with an outlet aperture at one side of the doorway, a return air duct with an inlet aperture at another second of the doorway and an intermediate air duct extending between the supply plenum and return air duct, and an air mover for moving an air stream across the doorway into the air curtain's respective inlet aperture to the return air duct through the intermediate air duct to the supply air plenum and out of the outlet aperture. The apparatus includes a heater in thermal communication with the air stream from at least one of the air curtains for warming the air stream of the particular air curtain, and a control unit controlling the operation of the heater. A first air sensor located in one of the relatively cool and warm air areas provides an air characteristic input to the control unit. A second air sensor located in contact with the air stream provides an air stream characteristic input to the control unit. The control unit continuously monitors the air characteristic input and the air stream characteristic input and operates the heater to maintain the temperature of the air stream at a point to the right of a line representing the mixing of the air stream with one or both of the air masses that is tangent to the psychrometric saturation curve.

In yet another exemplary embodiment of the present invention, a method is provided for maintaining a non-saturated air stream across a doorway between areas of relatively cool and warm air masses so as to prevent condensation and the formation fog or frost at the doorway. The air stream is generated by an air curtain including a supply air plenum with an outlet aperture at a first side of the doorway through which an air stream is forced across the doorway to an inlet aperture of a return air duct at a second side of the doorway. In this embodiment, the condition of the air stream and the condition of at least one of the relatively cool and warm ambient air areas are continuously monitored. The air stream is conditioned to maintain the temperature and humidity of the air stream at a point to the right of a line representing the mixing of the air stream with one or both of the air masses that is tangent to the psychrometric saturation curve, based on a humidity ratio of the vestibule.

In yet another exemplary embodiment, a method is provided for maintaining a non-saturated air stream across a doorway between areas of relatively cool and warm air masses so as to prevent condensation and the formation fog or frost at the doorway. The air stream is generated by an air curtain including a supply air plenum with an outlet aperture at a first side of the doorway. The air stream is forced through the aperture across the doorway to an inlet aperture of a return air duct at a second side of the doorway. The condition of the air stream and the condition of at least one of the relatively cool and warm ambient air areas are continuously monitored. The air stream is conditioned to maintain the temperature and humidity of the air stream at a point to the right of a line representing the mixing of the air stream with one or both of the air masses that is tangent to the psychrometric saturation curve, based on a humidity ratio of the doorway.

In yet another exemplary embodiment, a method is provided for controlling air flow in an air curtain arrangement having a plurality of air curtains. A humidity ratio is calculated for the air curtain arrangement based upon an intersection point between a warm side tangent line to a psychrometric saturating curve and a cold side tangent line to the curve. Air flow of at least one of the air curtains is adjusted based upon the calculated humidity ratio. A temperature of an air stream in at least one of the air curtains is maintained based upon an intersection point of a humidity ratio line based on the humidity ratio and at least of the warm and cold side tangent lines.

BRIEF DESCRIPTION OF DRAWINGS

The detailed description will refer to the following drawings, wherein like numerals refer to like elements, and wherein.

DETAILED DESCRIPTION

Figure 1:
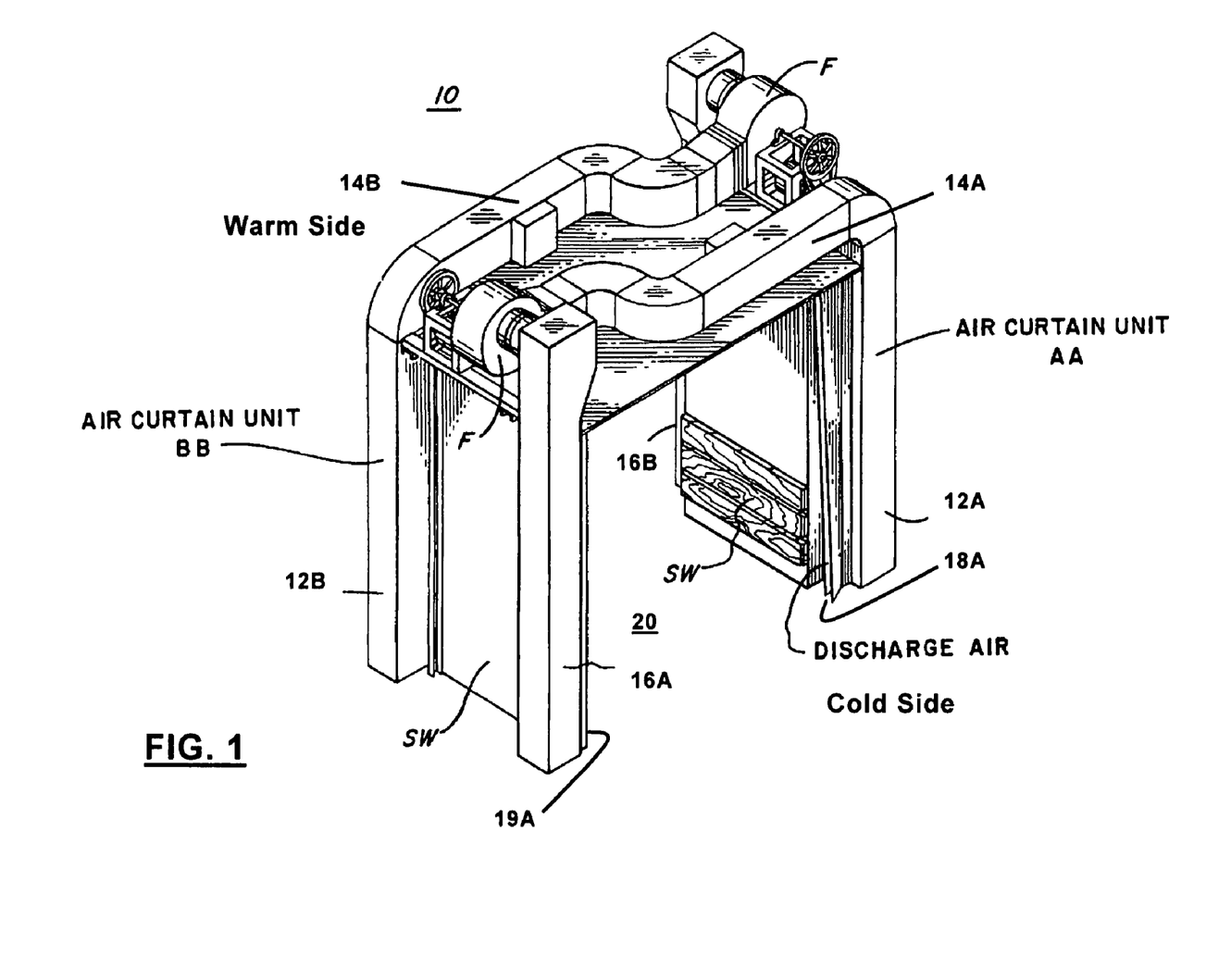
FIG. 1 shows a perspective view of one embodiment of a vestibule.

FIG. 1 shows a perspective view of one embodiment of an air curtain arrangement 10 according to the present invention. Embodiments of an air curtain arrangement may include one or more air curtain units (e.g., AA, BB in FIG. 1). As used herein, an air curtain unit (or air curtain) refers to an apparatus having at least a supply air plenum 12A, 12B with an outlet aperture 18A that discharges air across the doorway 20, a return air duct 16A, 16B with an inlet aperture (not shown) that receives the air discharged across the doorway 20, and an intermediate air duct 14A, 14B extending between the supply plenum 12A, 12B and return air duct 16A, 16B, or equivalent components. Air curtains may direct air across the doorway 20 horizontally, vertically, or otherwise. Air curtain arrangements having two or more air curtains are sometimes referred to as "vestibules." Vestibules having multiple air curtains may use different types of air curtains or air curtains in different configurations, or both. For example, a vestibule may include first and second horizontal air curtains that direct air in opposite directions across the doorway.

The embodiment of FIG. 1 includes first and second air curtain units AA, BB that each direct air horizontally across the doorway 20 in opposite directions. The air curtain arrangement 10 of FIG. 1 includes a control unit (not shown) that controls temperature of the air discharged across the doorway 20 by at least one of the air curtains AA, BB. In the embodiment shown in FIG. 1, an air mover, such as the fan F, directs air through the air curtains AA, BB. A heater (not shown) warms the air in the first air curtain AA (nearest the relatively cold side) to a temperature controlled by the control unit. In one embodiment, the heater (not shown) may be located in the intermediate air duct 14A, 14B near the fan F. In one embodiment, the heater heats the air only in the air curtain unit AA nearest the freezer. The control unit specifies a temperature for the heater that ensures that the vestibule operates below the psychrometric saturation curve to ensure that frost, ice, and fog do not form in the doorway 20. The control unit is electrically connected to the heater and may be positioned in any convenient location.

Figure 2:
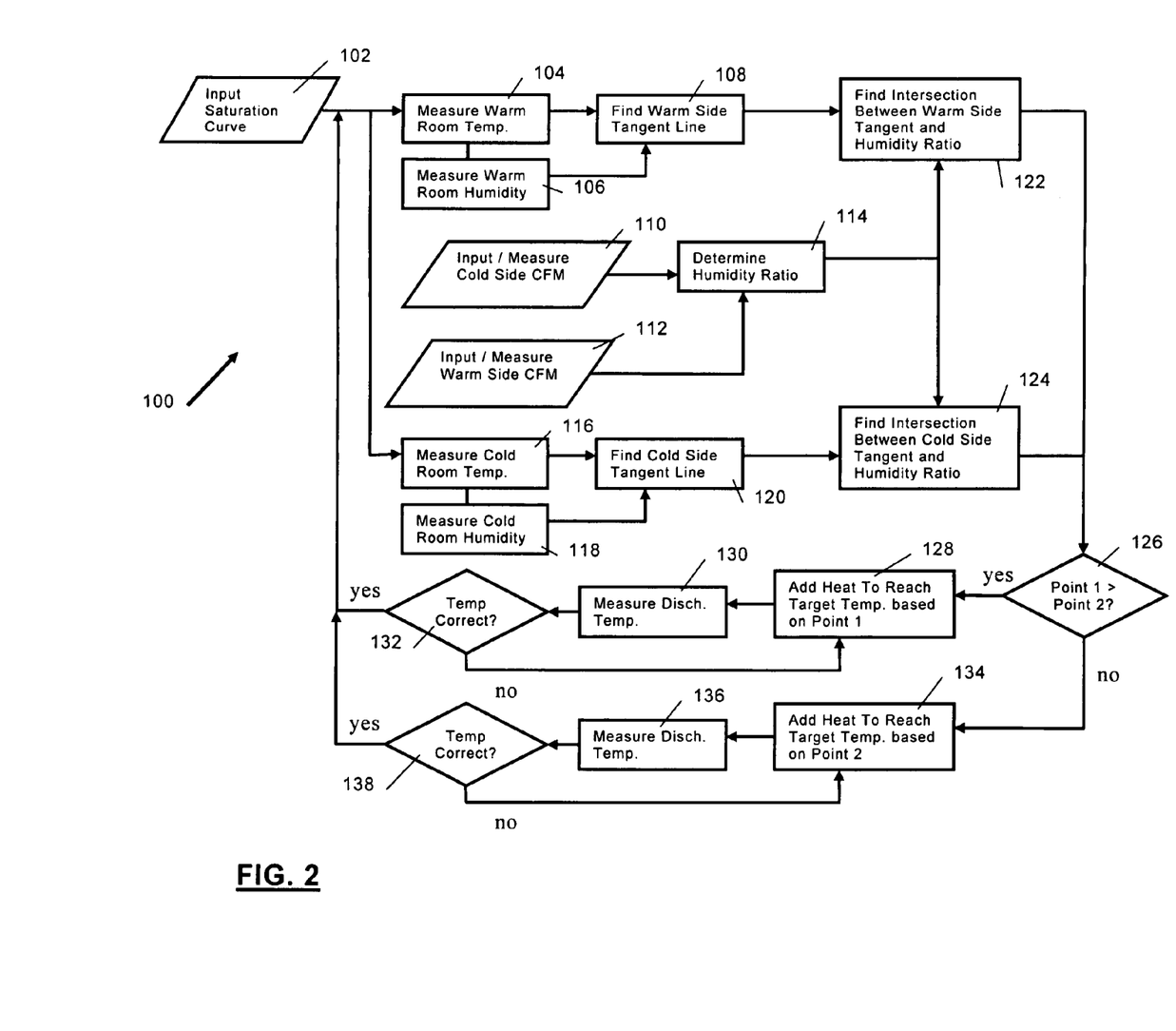
FIG. 2 shows a flow chart of one embodiment of the method of controlling temperature of an air stream discharged by an air curtain in a multiple air curtain vestibule.
Figure 3:
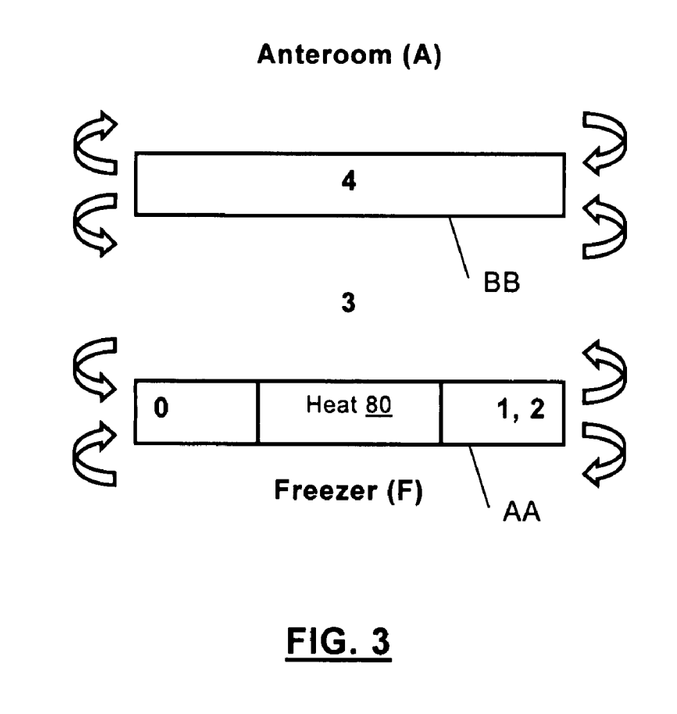
FIG. 3 shows a schematic view of the vestibule of FIG. 1.

FIG. 2 shows a flow chart of one embodiment of the method 100 of controlling temperature of an air stream discharged by an air curtain (e.g. AA, BB in FIG. 1) in a multiple air curtain vestibule 10. By way of example, the method 100 of FIG. 2 may be applied to a vestibule 10 having two air curtains AA, BB such as shown in FIG. 1. FIG. 3 shows a schematic view of the vestibule 10 of FIG. 1, for reference of the method 100 of FIG. 2. The exemplary embodiment of FIG. 3 includes two air curtains AA, BB across the doorway 20. The first air curtain AA is near the freezer F (i.e., the relatively cold side) and the second air curtain BB is near the anteroom A (i.e., the relatively warm side). Point 0 represents conditions (e.g., temperature and humidity) of the return air to the first air curtain AA. The first air curtain AA heats the returning air and discharges the air across the doorway 20. The first air curtain AA heats the air to a discharge temperature sufficient to prevent the formation of ice in the doorway 20. Points 1 and 2 represent different possible conditions of the discharge air, one of which points is selected by the method and system described herein. Point 3 represents a condition of air at a point between the first and second air curtains AA, BB. Point 4 represents a condition of air circulating in the second air curtain BB. In this embodiment, the second air curtain BB does not heat the air.

In the example method 100 of FIG. 2, a psychrometric saturation curve (also referred to as the saturation curve) is input 102 to a control unit. Saturation curves vary depending upon barometric pressure, so the saturation curve that is appropriate to the conditions in which the vestibule 10 operates is selected. In another embodiment, the barometric pressure may be calculated by a control unit using a pressure sensor input, and the control unit may calculate the saturation curve or select the curve from multiple curves representing different barometric pressures, which may be stored as data in memory of the control unit or external memory, for example.

One or more air characteristics are input to the control unit from the warm side A. In the embodiment shown in FIG. 2, the warm side temperature is measured 104, and the warm side humidity is measured 106, using sensors on the warm side A. The warm side temperature and humidity are input to the control unit. Based on the warm side temperature and humidity, the control unit calculates 108 a warm side tangent line to the psychrometric saturation curve.

Figure 4:
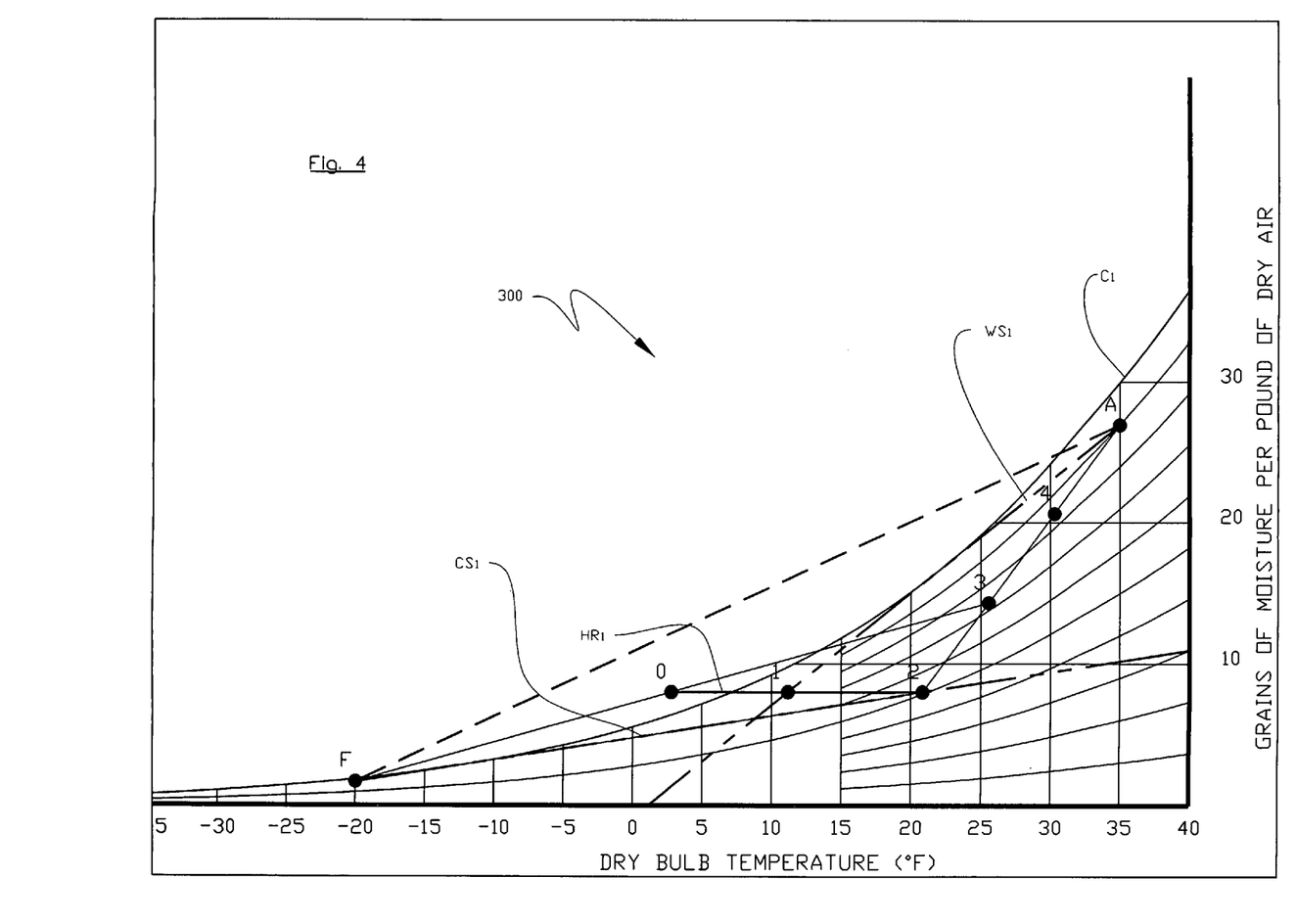
FIG. 4 shows psychrometric saturation curves with example data to illustrate the operation of the method of FIG. 2.
Figure 5:
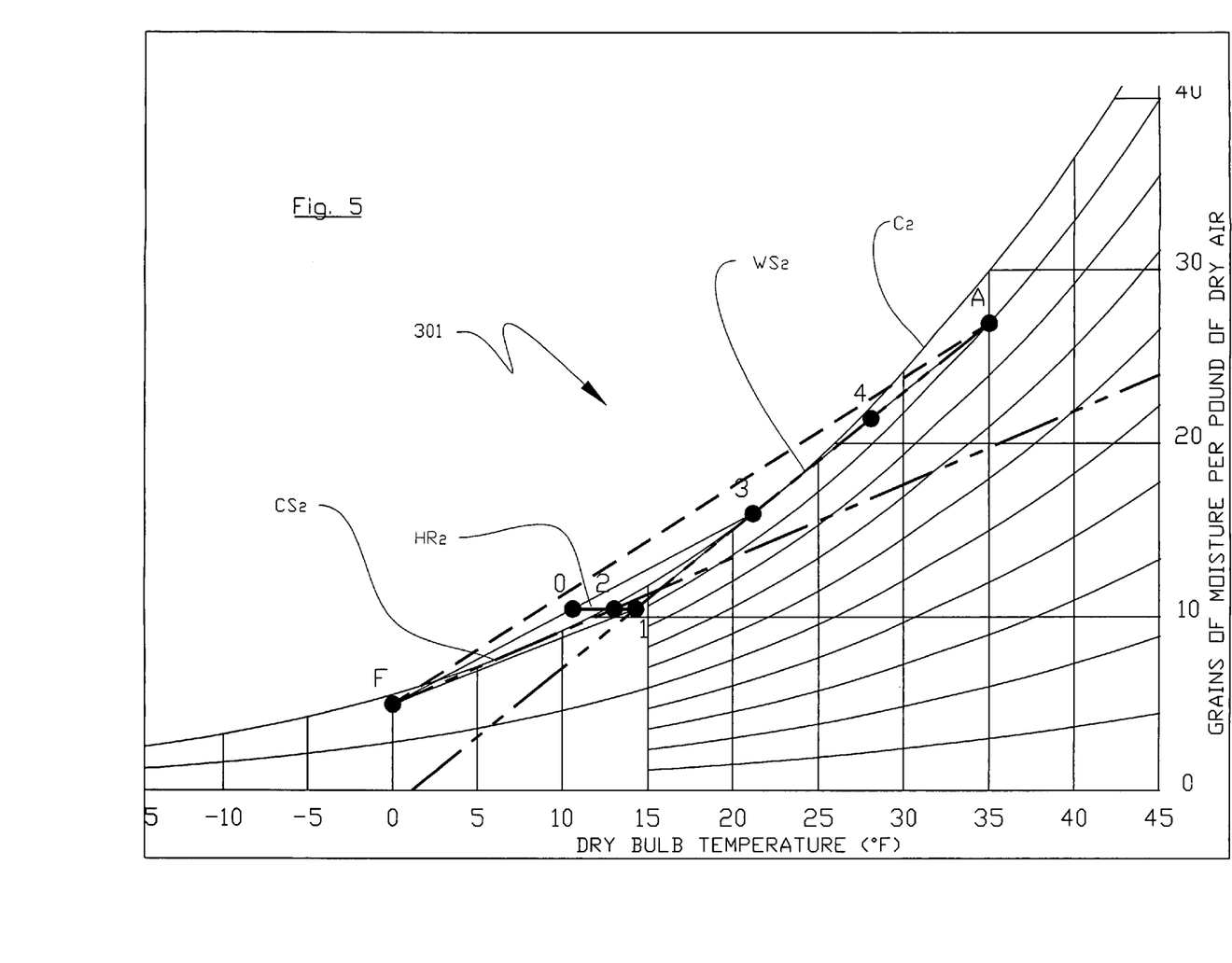
FIG. 5 shows psychrometric saturation curves with another example data to illustrate the operation of the method of FIG. 2.

FIGS. 4 and 5 show psychrometric saturation charts 300, 301 with example data to illustrate the operation of the method 100 of FIG. 2. Curves $C_1$, $C_2$ are illustrated in a manner that is commonly used in the art. In FIGS. 4 and 5, the points A and F represent the humidity and temperature of the relatively warm and cold sides (e.g., points A and F in FIG. 3), as plotted on the psychrometric saturation chart. The warm side conditions (point A) are the same for both FIGS. 4 and 5, but the cold side room is warmer in the example of FIG. 5 than it is in FIG. 4 (0 degrees Fahrenheit in FIG. 5 versus −20 degrees Fahrenheit in FIG. 4). In both FIGS. 4 and 5, the dashed lines $WS_1$, $WS_2$ passing through point A and point 1, which is tangent to the saturation curves $C_1$, $C_2$, represent the warm side tangent lines calculated at block 108 in FIG. 2. The lines $CS_1$, $CS_2$ represent the cold side tangent lines.

The cold side tangent lines $CS_1$, $CS_2$ pass through point F and Point 2, and are also tangent to the respective curves $C_1$, $C_2$. The dashed lines from point F to point A represent the mixing line of air between the relatively cold and warm sides (e.g., air moving between point A and point F on the schematic of FIG. 3) in the absence of heat added by at least one of the air curtains AA, BB in the vestibule 10. In both examples, the A-F mixing lines lie above the saturation curves $C_1$, $C_2$, which means that ice, water, or fog could form in the doorway 20 without the addition of heat.

Referring to FIG. 2, the air flow from the warm side air curtain BB is input 112 to the control unit, and the air flow from the cold side air curtain AA is input 110 to the control unit. In the embodiment shown, the air flow is input as a volumetric air flow value in cubic feet per minute (CFM). In one embodiment, the air flow is input to the control unit manually, as a fixed value for the vestibule 10. The related examples shown in FIGS. 4 and 5 illustrate an embodiment having two air curtains AA, BB each having the same air flow (e.g., each having the same-sized, fixed speed fans). In a two-curtain arrangement in which each air curtain AA, BB has the same, fixed air flow, the humidity ratio HR, line is illustrated on the psychrometric saturation chart as a horizontal line one-quarter of the way between points F and A, as shown in FIGS. 4 and 5. The fixed air flow volume for each air curtain AA, BB is input 110, 112 (for example, into a control unit (50 in FIG. 6) that performs the method 100) as fixed values for each air curtain AA, BB. In other embodiments, the air flow may be different for each air curtain AA, BB and/or may change during operation. Sensors (not shown) may be used to monitor the actual air flow and may provide air flow input data to the control unit (50 in FIG. 6). The control unit (50 in FIG. 6) defines 114 horizontal humidity ratio line $HR_1$, $HR_2$ based on the air flow across the vestibule 10, which can be adjusted based upon the size of fans in the air curtain AA. These humidity ratio lines $HR_1$, $HR_2$ are shown in FIGS. 4 and 5 as horizontal lines at point 0 and passing through points 1 and 2. Stated differently, point 1 is defined as the intersection on the psychrometric saturation chart of the warm side tangent line $WS_1$, $WS_2$ and the humidity ratio line $HR_1$, $HR_2$. Point 2 is defined as the intersection of the cold side tangent line $CS_1$, $CS_2$ and the humidity ratio line $HR_1$, $HR_2$.

Air characteristics of the cold room F are also measured and input to the control unit. In the embodiment of FIG. 2, the air characteristics of temperature and humidity are measured. The cold room temperature is measured 116 and input to the control unit. The cold room humidity is measured 118 and input to the control unit. Based on the cold room temperature and humidity, the control unit determines 120 a cold side tangent line $CS_1$, $CS_2$ to the saturation curve $C_1$, $C_2$. In the example plots of FIGS. 4 and 5, these cold side tangent lines $CS_1$, $CS_2$ are represented by lines from point F through point 2, which is tangent to the curve $C_1$, $C_2$.

First and second temperatures are calculated based on the cold side and warm side tangent lines $CS_1$, $CS_2$, $WS_1$, $WS_2$. A first temperature is determined 122 by the intersection point between the warm side tangent line $WS_1$, $WS_2$ and the humidity ratio line $HR_1$, $HR_2$, which is shown as point 1 in FIGS. 4 and 5. A second temperature is determined 124 by the intersection point between the cold side tangent line $CS_1$, $CS_2$ and the humidity ratio line $HR_1$, $HR_2$, which is shown as point 2 in FIGS. 4 and 5.

The control unit uses the larger of the first and second temperatures to determine how much heat to add to the air curtain AA. The selected temperature (point 1 or 2) is the air discharge temperature of the air curtain AA, shown by points 1 and 2 on the schematic of FIG. 3. In the example method 100 of FIG. 2, the control unit determines 126 whether the first or second temperature is greater. If the first temperature is greater ("yes" branch at block 126), then the control unit causes the heater to add heat 128 based on the first temperature. In this embodiment, heat is added at a preset increment. The air discharge temperature is measured 130. The control unit determines 132 whether the air stream temperature has reached a target temperature based on the first temperature. If the target temperature is not yet reached ("no" branch at block 132), the control unit continues to add heat 128 until the target temperature is reached. Once the target temperature is reached ("yes" branch at block 132), the method 100 returns to the steps of measuring the warm side and cold side temperature and humidity (blocks 104, 106, 116, 118). In one embodiment, the control unit causes the heater 80 to add heat until the air stream temperature exceeds the first temperature by a predetermined amount (e.g., 10 degrees greater than the first temperature). If the second temperature is greater ("no" branch at block 126), then the control unit causes the heater to add heat 134, and the air discharge temperature is measured 136. The control unit determines 138 whether the air discharge temperature has reached a target temperature based on the second temperature. If the target temperature is not yet reached ("no" branch at block 138), the control unit causes the heater 80 to continue to add heat 134 until the target temperature is reached. Once the target temperature is reached ("yes" branch at block 138), the method 100 returns to the steps of measuring the warm side and cold side temperature and humidity (blocks 104, 106, 116, 118).

As described with respect to blocks 126, 128, 130, 132, 134, 136, 138, the control unit warms the air stream to a target temperature based on the greater of the first and second temperatures. The target temperature is at least as great as the greater of the first and second temperatures. In one embodiment, the target temperatures are greater than the first and second temperatures by a margin factor (e.g., 10 degrees Fahrenheit). This margin factor ensures that the mixing lines remain below the saturation curves (e.g., $C_1$, $C_2$), and that frost, ice, and fog does not form in the doorway 20. In the example of FIG. 4, the second temperature, represented by the intersection of the cold side tangent line $CS_1$ and the humidity ratio line $HR_1$ (point 2), is greater than the first temperature, so the control unit causes the heater to warm the discharge air stream to a temperature that is at least as great as the second temperature. In the example of FIG. 5, the first temperature, represented by the intersection of the warm side tangent line $WS_2$ and the humidity ratio line $HR_2$ (point 1), is greater than the second temperature, so the control unit warms the discharge air stream to a temperature that is at least as great as the first temperature.

Figure 6:
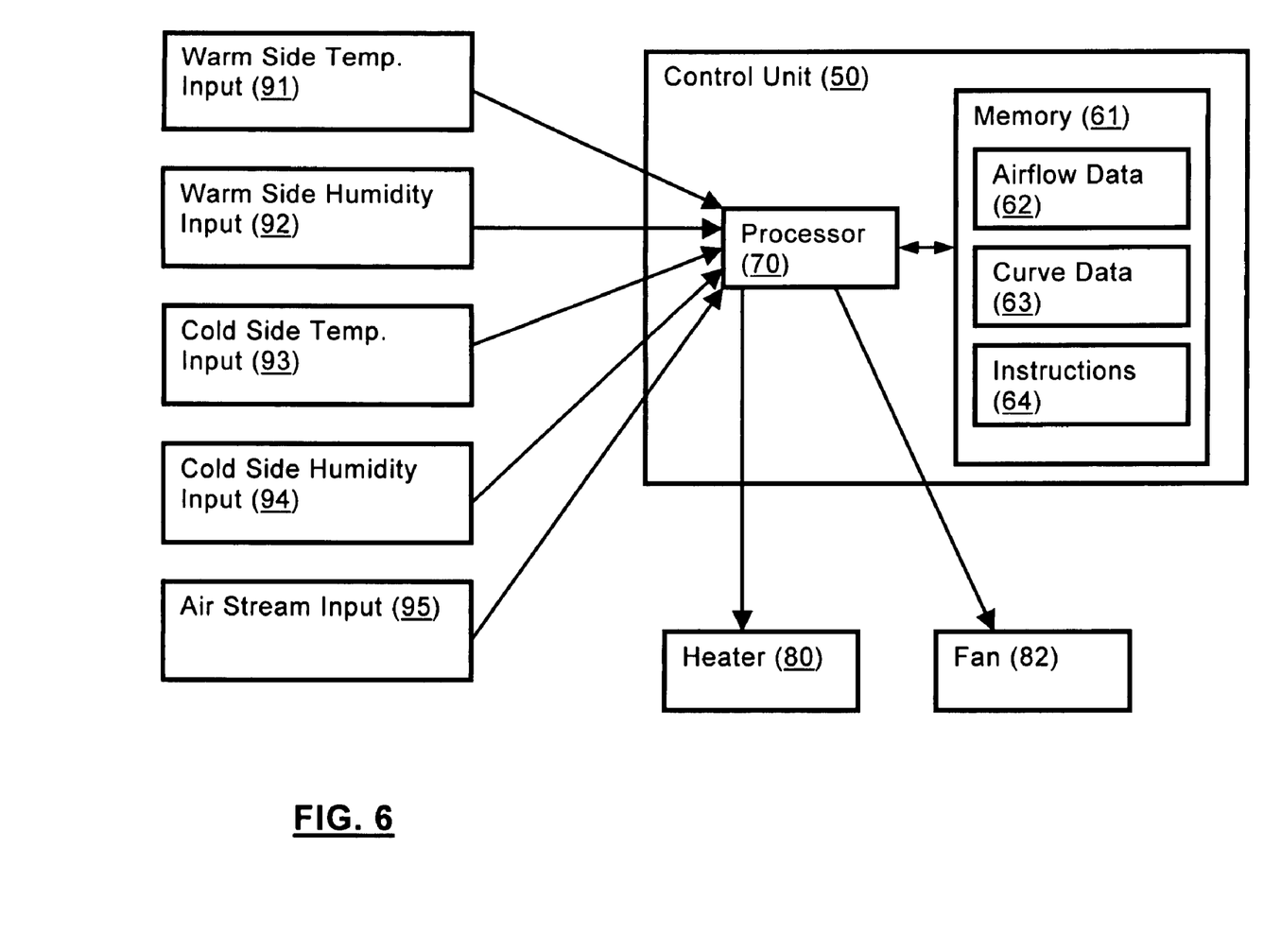
FIG. 6 shows a block diagram of a control unit that may be used to implement the method described with respect to FIG. 2.

FIG. 6 shows a block diagram of a control unit 50 that may be used to implement the method 100 described with respect to FIG. 2. The control unit 50 includes a processor 70 and a memory 61. In this embodiment, a storage arrangement such as memory 61 stores instructions 64 to be executed by the processor 70 to perform the functions to control temperature of airflow in the vestibule 10, such as the functions specified in the method 100 described with respect to FIG. 2. In the embodiment shown, the processor 70 receives air characteristic inputs 91-94 from one or more air characteristic sensors described herein, including a warm side temperature input 91, a warm side humidity input 92, a cold side temperature input 93, and a cold side humidity input 94. Data input from the sensors may be stored, for example, in the memory 61. The memory 61 may also store values such as the saturation curve data 63 and the airflow data 62 described in the example of FIG. 2. Based upon the air characteristic inputs 91-94, the instructions cause the processor 70 to send a signal to the heater 80 of the air curtain AA to control temperature of the airflow in the vestibule 10. In addition, the processor 70 receives an air stream input 95 from an air stream sensor, such as a temperature sensor, that measures the air stream. In one embodiment, the heater 80 is positioned in the air curtain (e.g., AA in FIG. 1) nearest the freezer F. The control unit 50 continuously monitors the air stream input 95 to adjust the air stream temperature in real time to maintain the vestibule 10 in a non-saturated condition. The controller 70 may also control one or more fans 82 in one or more of the air curtains AA, BB as described further with respect to FIG. 10.

Figure 7:
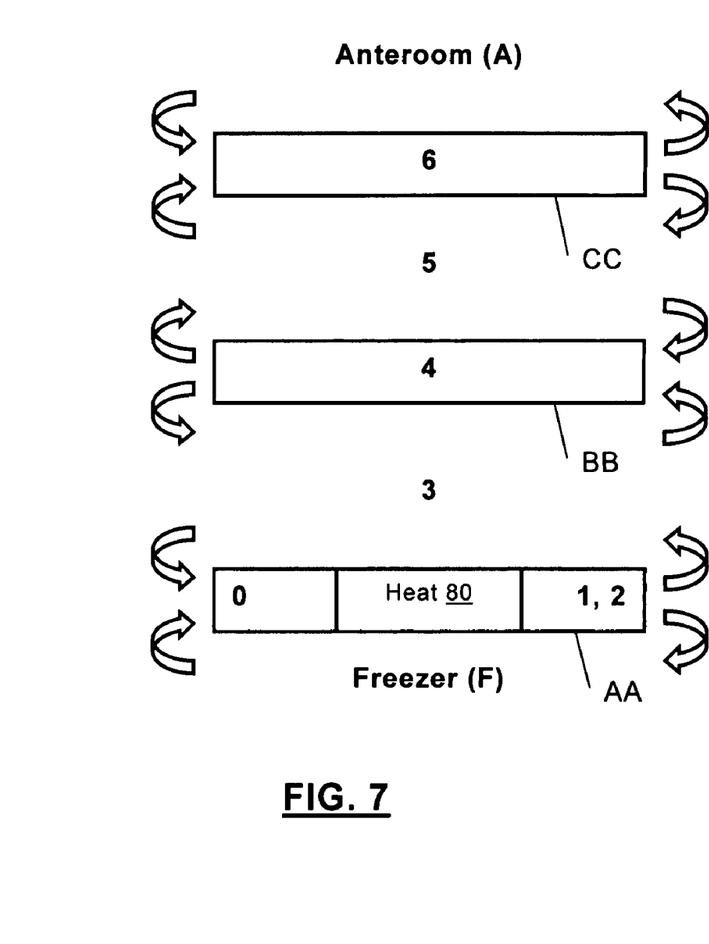
FIG. 7 shows a schematic of an exemplary triple air curtain arrangement between a freezer and an anteroom, having a heater in the first air curtain.

The present invention may be extended beyond double air curtain embodiments to include embodiments having multiple air curtains. FIG. 7 shows a schematic of an exemplary triple air curtain arrangement between a freezer F and an anteroom A, having a heater 80 in the first air curtain AA. Point 0 represents conditions at a point at an intake (e.g., 19A in FIG. 1) of the first air curtain AA. Points 1 and 2 represent conditions at a point at a discharge (e.g., 18A in FIG. 1) of the first air curtain AA. Point 3 represents conditions at a point between the first and second air curtains AA, BB. Point 4 represents conditions at a point within the second air curtain BB. Point 5 represents conditions at a point between the second and third air curtains BB, CC. Point 6 represents conditions at a point within the third air curtain CC.

Figure 8:
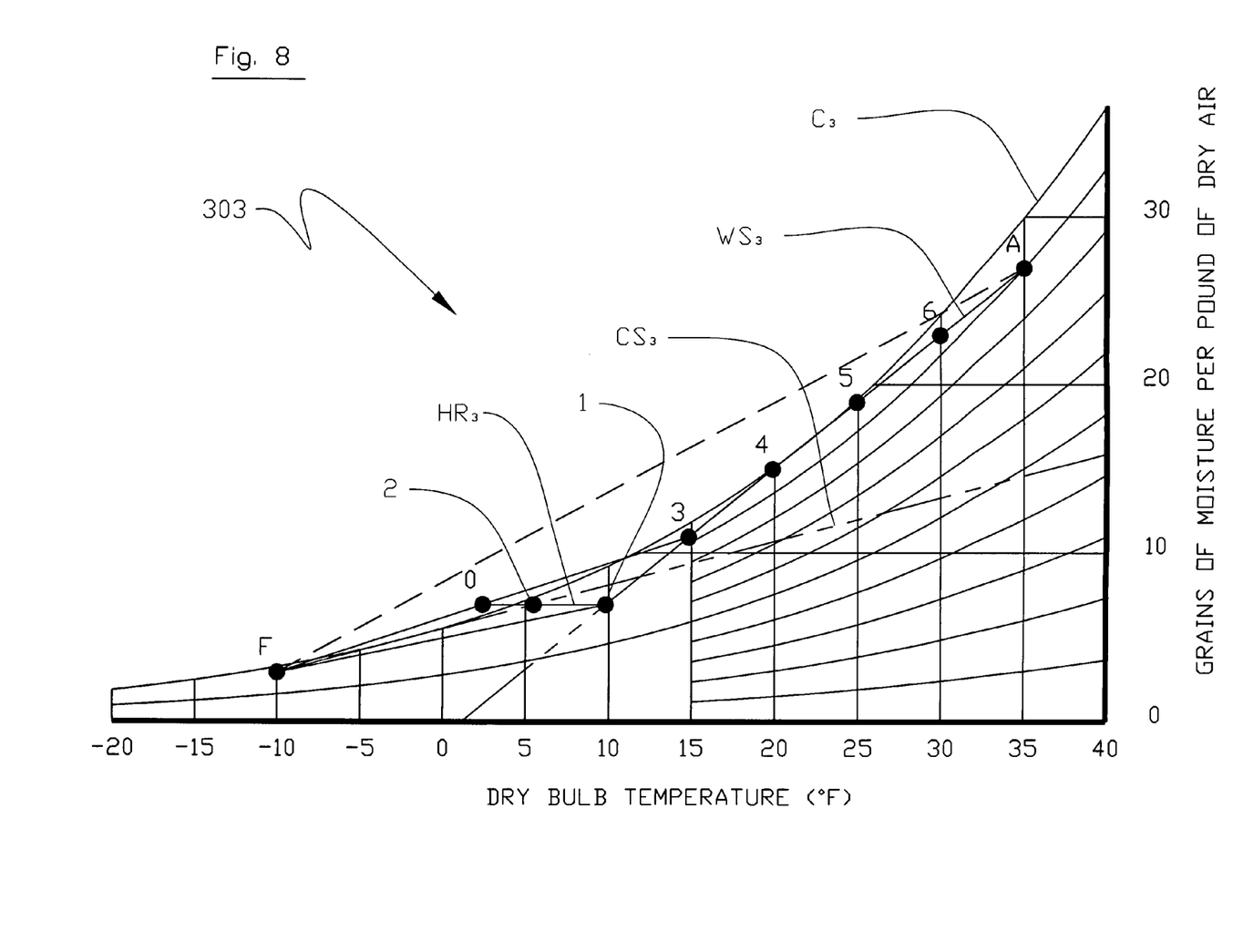
FIG. 8 shows an example psychrometric saturation chart for a triple air curtain arrangement.
Figure 9:
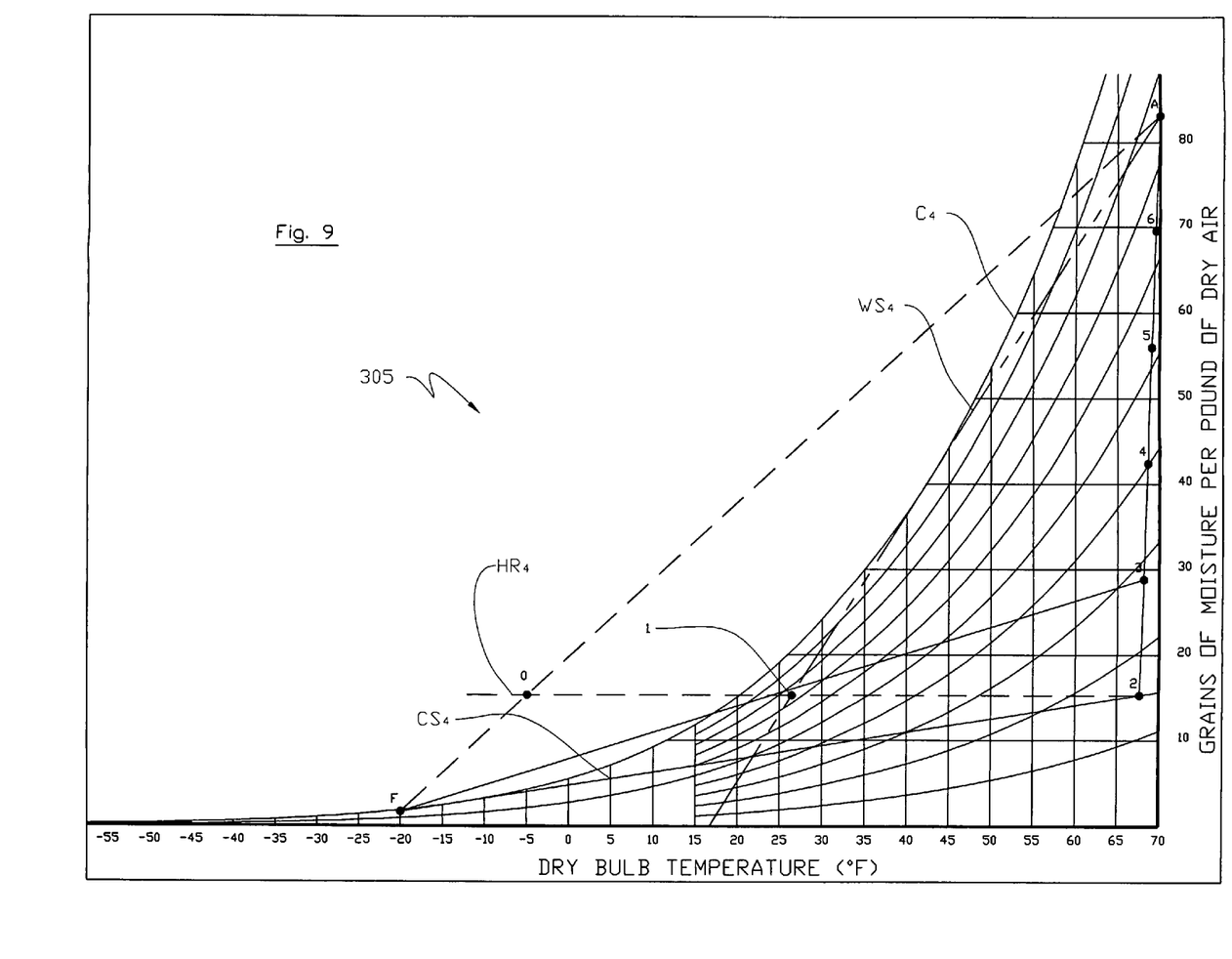
FIG. 9 shows an another example psychrometric saturation chart for a triple air curtain arrangement.

FIGS. 8 and 9 show example psychrometric saturation charts 303, 305 for a triple air curtain arrangement. Points 0-6 in FIG. 7 correspond to points 0-6 on the saturation curves of FIGS. 8 and 9. FIG. 8 reflects an example in which the freezer is maintained at −10 degrees Fahrenheit, and the anteroom is 35 degrees Fahrenheit.

In the example of FIG. 8, the warm side tangent line $WS_3$ is illustrated as the dashed line passing through point A, tangent to the curve $C_3$. The cold side tangent line $CS_3$ is illustrated as the dashed line passing through point F, tangent to the curve $C_3$. The humidity ratio in this example is determined based upon the relative airflow of the air curtains AA, BB, CC, and is represented by the horizontal humidity ratio line $HR_3$ passing through point 0. Point 1 represents the intersection of the humidity ratio line $HR_3$ and the warm side tangent line $WS_3$. Point 2 represents the intersection of the humidity ratio line $HR_3$ and the cold side tangent line $CS_3$. In applying the method 100 of FIG. 2 to this example, point 1 (approximately 10 degrees Fahrenheit) is used to determine the target temperature, because point 1 is greater than point 2. Heat is added to the vestibule (e.g., at the first air curtain AA) based upon this target temperature.

FIG. 9 reflects an example psychrometric saturation chart 305 for which point 2 is greater than point 1, due to the operating conditions of the vestibule. In the example of FIG. 9, the warm side tangent line $WS_4$ is illustrated as the dashed line passing through point A, tangent to the curve $C_4$. The cold side tangent line $CS_4$ is illustrated as the dashed line passing through point F, tangent to the curve $C_4$. As with the example of FIG. 8, the humidity ratio in this example is determined based upon the relative airflow of the air curtains AA, BB, CC, and is represented by the horizontal humidity ratio line $HR_4$ passing through point 0. Point 1 represents the intersection of the humidity ratio line $HR_4$ and the warm side tangent line $WS_4$. Point 2 represents the intersection of the humidity ratio line $HR_4$ and the cold side tangent line $CS_4$. In applying the method 100 of FIG. 2 to this example, point 2 (approximately 68 degrees Fahrenheit) is used to determine the target temperature, because point 2 is greater than point 1 in this example. Heat is added to the vestibule (e.g., at the first air curtain AA) based upon this target temperature.

Figure 10:
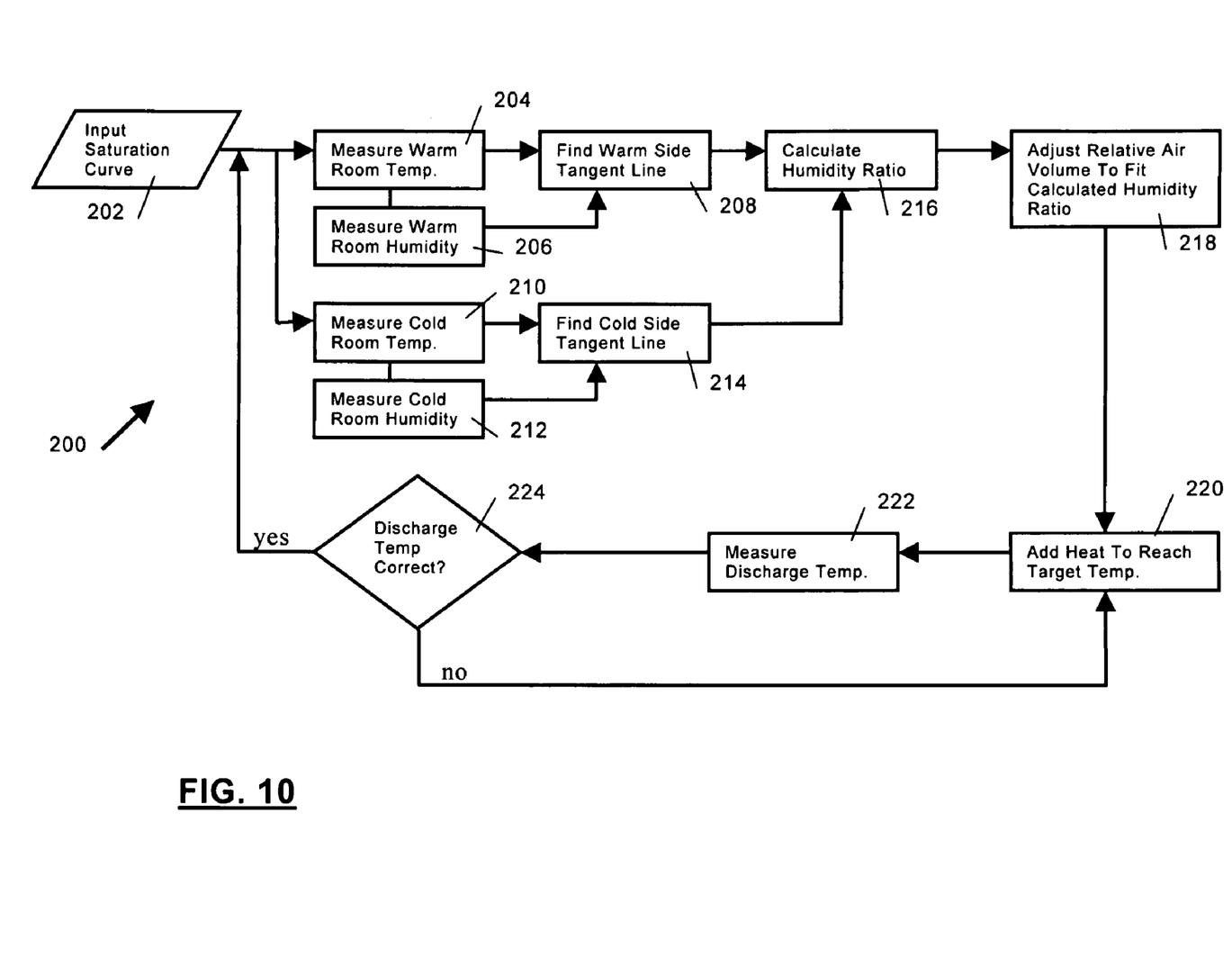
FIG. 10 shows a flow chart of another exemplary embodiment of a method of controlling a conditioned vestibule by varying airflow among separate air curtains.

FIG. 10 shows a flow chart of another exemplary embodiment of a method 200 of controlling a conditioned vestibule 10 by varying airflow among the separate air curtains AA, BB, CC. Air flow volume may be varied, for example, by using variable-speed fans in one or more of the air curtains AA, BB, CC. Depending upon the conditions, the control unit 50 may adjust the relative air speed of the fans dynamically to adjust the humidity ratio to minimize the amount of heat that the first air curtain AA must add, thereby optimizing the efficiency of the air curtain arrangement. For simplicity, each of the previous examples of double and triple air curtains are illustrated as having substantially the same air discharge volume for each air curtain AA, BB, CC (e.g., varies less than 25%). The humidity ratio lines $HR_1$, $HR_2$, $HR_3$, $HR_4$, defined on the example psychrometric saturation charts depend upon each air curtain's relative volume of air flow.

In the embodiment of FIG. 10, a saturation curve is input 202 into the control unit 50. Warm room temperature and humidity are measured 204, 206. Cold room temperature and humidity are measured 210, 212. A warm side tangent line is determined 208 based on the warm side temperature and humidity, and a cold side tangent line is determined 214 based on the cold side temperature and humidity. In the example of FIG. 10, a humidity ratio is calculated 216 as a horizontal line on the psychrometric saturation chart passing through the point defined by the intersection of the warm and cold side tangent lines (point 2* in FIG. 11). The relative air volume of the air curtains (e.g., AA, BB, CC) is adjusted 218 to create a humidity ratio equal to the ratio that was calculated 216. Heat is added 220 to reach a target temperature based on the calculated humidity ratio. By adjusting the relative air discharge volumes at the air curtains (e.g., AA, BB, CC) and thereby adjusting the humidity ratio, the required amount of heat may be decreased or even minimized.

As with the embodiment described with respect to FIG. 2, heat added to arrangement may be adjusted dynamically. An air discharge temperature is measured 222. If the air discharge temperature is the correct target temperature ("yes" branch at block 224), then the method 200 repeats itself. If the air discharge temperature is not correct ("no" branch at block 224), then the correct amount of heat is added 220. As with other embodiments described herein, the amount of heat added may include a buffer (e.g., 10% above the calculated temperature) to ensure that the operating conditions of the air curtain arrangement remain below the saturation curve.

In one embodiment, the air flow is adjusted dynamically based upon changing conditions in the vestibule 10. Air flow may be adjusted, for example, by controlling variable-speed fans in one or more of the individual air curtains AA, BB, CC. As the warm side or cold side tangent lines change, for example, the desired humidity ratio changes thereby requiring adjustment of the relative volumetric air flow of the individual air curtains AA, BB, CC. Also, air flow sensors (not shown) may be used to monitor the actual air flow across the vestibule 10 and to adjust fan speed (or other air flow control) based on the measured air flow.

Figure 11:
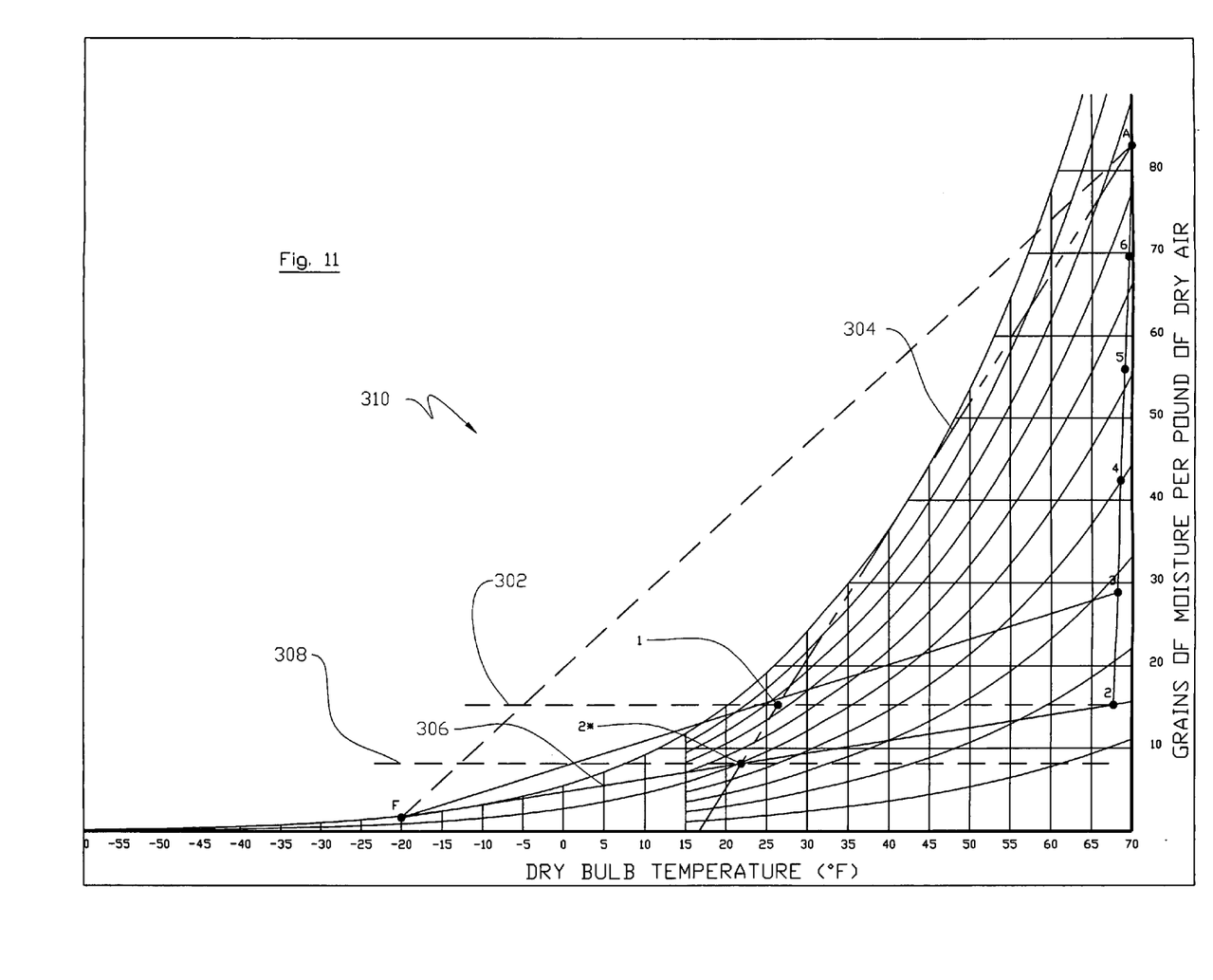
FIG. 11 shows an example psychrometric saturation chart for a triple air curtain arrangement illustrating the method of FIG. 10.

FIG. 11 shows an example psychrometric saturation chart 310 for a triple air curtain arrangement illustrating the method 200 of FIG. 10. The example air curtain arrangement is positioned between a freezer F at −20 degrees Fahrenheit and an anteroom A at 70 degrees Fahrenheit. The warm side tangent line 304 and the cold side tangent line 306 are shown on the chart 310. Dashed line 302 represents the even air flow humidity ratio. This would be the humidity ratio of the arrangement if each of the three air curtains AA, BB, CC had a fixed and equal air flow. Points 1 and 2 represent the intersections of the even air flow humidity ratio line 302 with the warm side tangent line 304 and the cold side tangent line 306, respectively. At low freezer temperatures, such as the −20 degrees Fahrenheit of this example, the cold side tangent line 306 begins to flatten more noticeably. As a result, the temperature difference between points 1 and 2 is larger. To avoid ice formation at this humidity ratio, sufficient heat would have to be added based on point 2, as the larger of the two temperatures 1, 2. In this example, point 2 is at a much warmer temperature than point 1, which would require addition of substantial heat.

To minimize the amount of heat required to be added, relative air flow in the air curtains AA, BB, CC is adjusted to lower the humidity ratio line closer to (or, in the embodiment shown, exactly at) the intersection of the warm side tangent line 304 and the cold side tangent line 306. The new humidity ratio line is illustrated as a dashed line 308, and passes through the intersection point 2*. In the embodiment of FIG. 11, the humidity ratio is lowered by increasing the air flow of the freezer-side air curtain AA relative to at least one of the other two air curtains BB, CC. As a result, less heat is required to be added to bring the air curtain arrangement to the target temperature 2*, than would be required to reach point 2, or even point 1 in this example.

In other embodiments, the humidity ratio is adjusted from an even flow humidity ratio, but is not lowered all the way to the intersection point 2*. In such embodiments, points 1 and 2 are separate points along the humidity ratio line, as described with respect to FIGS. 4 and 5. Heat is added to the arrangement based on the larger of points 1 and 2, as described with respect to FIG. 3. In this manner, the efficiency of the arrangement is increased even though the humidity ratio is not set all the way to the intersection point of the cold and warm side tangent lines.

Although the present invention has been described with respect to particular embodiments thereof, variations are possible. The present invention may be embodied in specific forms without departing from the essential spirit or attributes thereof. In addition, although aspects of an implementation are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; other forms of RAM or read-only memory (ROM); or any other type of storage arrangement. Also, examples of psychrometric saturation charts are illustrated in standard convention with dry bulb temperature on the horizontal axis, increasing left to right, and humidity on the vertical axis increasing bottom to top. Accordingly, a point to the right of a line on this plot has a higher temperature than the line itself, at the same humidity. In other embodiments, the psychrometric saturation chart could be prepared with a different convention. It is desired that the embodiments described herein be considered in all respects illustrative and not restrictive and that reference be made to the appended claims and their equivalents for determining the scope of the invention.

What is claimed is:

1. An air curtain arrangement for a cold storage doorway, comprising:
   a discharge means that discharges an air stream across a doorway having a cold side and a warm side;
   a heater that warms the air stream;
   a control unit that operates the heater to maintain an air stream temperature;
   an air return means that receives the air discharged across the opening; and
   an air stream temperature sensor that provides an air stream temperature input to the control unit;
   wherein the control unit continuously monitors the air stream temperature, and operates the heater to maintain the air stream temperature at the greater of (1) a first temperature represented by an intersection on a psychrometric saturation chart of a warm side tangent line to a psychrometric saturation curve and a humidity ratio line based on a humidity ratio, and (2) a second temperature represented by an intersection of a cold side tangent line to the curve and the humidity ratio line, wherein the humidity ratio is predetermined based upon an intersection of the warm and cold side tangent lines to the psychrometric saturation curve on a psychrometric saturation chart.

2. The air curtain arrangement of claim 1,
   further comprising warm and cold side temperature sensors that sense temperatures of the warm and cold sides, respectively, and provide inputs to the control unit, and
   wherein the control unit continuously monitors the warm and cold side temperatures and operates the heater based on the warm and cold side temperatures.

3. The air curtain arrangement of claim 2,
   further comprising warm and cold side humidity sensors that sense humidity of the warm and cold sides, respectively, and provide inputs to the control unit, and
   wherein the control unit continuously monitors the warm and cold side humidity and operates the heater based on the warm and cold side humidity.

4. The air curtain arrangement of claim 1,
   further comprising a volumetric air flow control that controls flow of the air stream to maintain the air curtain arrangement at the humidity ratio calculated based on warm and cold side tangent lines to a psychrometric saturation curve.

5. An air curtain arrangement for a cold storage doorway, comprising:
   means for directing a plurality of air streams across the doorway having a relatively warm side and a relatively cold side; and
   means for maintaining a temperature at the air stream based on a predetermined humidity ratio associated with the doorway, by controlling relative volumetric airflow of the plurality of air streams,
   wherein said means for maintaining comprises:
       means for determining a temperature and humidity of a warm side and a cold side of the doorway; and
       means for setting the temperature based on the temperature and humidity of the cold side and warm side by determining a first and a second temperature based, respectively, on a warm side tangent line and a cold side tangent line to a psychrometric saturation curve, and based on the humidity ratio, and setting the air stream temperature based on a greater of the first and second temperatures.

6. The air curtain arrangement of claim 5, wherein the means for maintaining comprise means for warming the air stream to the temperature, and means for controlling the means for warming.

7. The air curtain arrangement of claim 5, wherein the means for determining comprises means for sensing the humidity and temperature of the warm side and cold side during operation of the air curtain arrangement.

8. The air curtain arrangement of claim 5, wherein the means for maintaining comprises means for controlling the airflows based upon temperature and humidity of the warm and cold side and upon a barometric pressure.

9. The air curtain arrangement of claim 5, wherein the means for maintaining comprises means for controlling the relative volumetric airflows based upon an intersection point on a psychrometric saturation chart of warm and cold side tangent lines to a saturation curve, wherein the warm and cold side tangent lines are based, respectively, on air characteristics of the warm and cold sides.

10. The air curtain arrangement of claim 5,
    further comprising sensing the relative volumetric airflows and air characteristics during operation of the air curtain arrangement; and
    wherein the means for maintaining comprises means for dynamically controlling the relative volumetric airflows during the operation of the air curtain arrangement.

11. A method of controlling air stream temperature of an air curtain used in connection with an air curtain arrangement for a cold storage doorway that separates relatively warm and cold sides, the method comprising:
  continuously monitoring warm and cold side temperatures;
  determining a warm side tangent line that is tangent to a saturation curve on a psychrometric saturation chart, using the warm side temperature and a warm side humidity;
  determining a cold side tangent line that is tangent to the saturation curve, using the cold side temperature and a cold side humidity;
  determining a humidity ratio based upon an intersection point on the saturation chart of the warm and cold side tangent lines;
  determining a first temperature represented by an intersection of the warm side tangent line and a humidity ratio line based on the humidity ratio;
  determining a second temperature represented by an intersection of the cold side tangent line and the humidity ratio line;
  directing the air stream across the doorway; and
  maintaining the air stream at the greater of the first and second temperatures.

12. The method of claim 11, further comprising controlling the humidity ratio by controlling volumetric airflow in the air curtain arrangement.

13. The method of claim 12, wherein the controlling the volumetric airflow comprises controlling volumetric airflow of the air stream relative to another air stream in the arrangement.

14. A conditioned vestibule for a cold storage doorway, comprising:
  first and second air curtains positioned adjacent each other, wherein the air curtains each direct an air stream across a doorway that separates a relatively warm side from a relatively cold side;
  one or more sensors that sense an air characteristic of at least one of the warm side and the cold side;
  an air stream sensor that senses an air characteristic of the air stream and provides an air stream input to the control unit; and
  a control unit that operates a heater to maintain the air stream of at least one of the air curtains at a temperature based on a humidity ratio of the vestibule, wherein the humidity ratio is based on the air curtains' relative volumetric airflow, wherein the control unit receives an air characteristic input from the one or more sensors and continuously monitors the air characteristic input, and operates the heater to maintain the air stream temperature based on the greater of (1) a first temperature represented by an intersection on a psychrometric saturation chart of a warm side tangent line to a psychrometric saturation curve and a humidity ratio line based on the humidity ratio, and (2) a second temperature represented by an intersection of a cold side tangent line to the curve and the humidity ratio line.

15. The vestibule of claim 14,
  wherein the one or more sensors comprise a temperature sensor that senses temperature on at least one of the warm and cold sides, and
  wherein the air stream sensor senses the air stream temperature.

16. The vestibule of claim 14,
  wherein the first air curtain is positioned near the relatively cold side, and the second air curtain is positioned near the relatively warm side, and
  wherein the control unit maintains the air stream temperature of the first air curtain.

17. The vestibule of claim 16,
  further comprising one or more sensors that sense temperature and humidity on the warm side and the cold side and provide inputs to the control unit, and
  wherein the warm side tangent line and cold side tangent line are based, respectively, on the warm and cold side temperature and humidity sensed by the at least one sensor.

18. The vestibule of claim 14, wherein the control unit controls relative airflow of at least one of the air streams to control the humidity ratio.

19. The vestibule of claim 18, wherein the control unit controls the relative airflow to maintain the humidity ratio based upon air characteristics of warm and cold sides.

20. A method of maintaining an air stream temperature of an air curtain in a doorway between a relatively cold side and a relatively warm side, the method comprising:
  continuously monitoring a temperature and a humidity of a relatively warm and a relatively cold side of a doorway comprising an air curtain that directs an air stream across the doorway;
  determining warm and cold side tangent lines based, respectively, on the warm and the cold side temperature and humidity, and
  maintaining the air stream at a temperature above the greater of first and second temperatures corresponding, respectively, to intersections on a psychrometric saturation chart of the warm and cold side tangent lines with a humidity ratio line based on a predetermined humidity ratio of mixed air in the air curtain.

21. A control unit for controlling temperature of an air stream directed across a doorway by one or more air curtains that are part of an air curtain arrangement positioned across the doorway separating relatively warm and cold air masses, the control unit comprising:
  a processor; and
  a storage arrangement that stores computer-executable instructions for execution by the processor to control operation of the air curtain arrangement, wherein the instructions comprise instructions for:
    continuously monitoring an air characteristic of at least one the relatively warm and cold air masses,
    continuously monitoring an air stream temperature, and
    operating a heater to warm the air stream temperature based on the greater of (1) a first temperature defined by an intersection of a warm side tangent line and a humidity ratio line, and (2) a second temperature defined by an intersection of a cold side tangent line and the humidity ratio line.

22. An apparatus for forming an air stream across a doorway between areas of relatively cool and warm air masses including a supply air plenum with an outlet aperture at a first side of the doorway, a return air duct with an inlet aperture at a second side of the doorway and an intermediate air duct extending between the supply plenum and return air duct, the apparatus comprising:
  an air mover for moving an air stream across the doorway into the inlet aperture to the return air duct through the intermediate air duct to the supply air plenum and out of the outlet aperture;
  a heater in thermal communication with the air stream for warming the air stream;
  a control unit controlling the operation of the heater;
  a first air sensor located in one of the relatively cool and warm air areas providing an air characteristic input to the control unit; and a second air sensor located in contact with the air stream providing an air stream characteristic input to the control unit;

wherein the control unit continuously monitors the air characteristic input and the air stream characteristic input and operates the heater to maintain the temperature of the air stream at a temperature that is at least as great as the greater of (1) a first temperature defined by an intersection of a warm side tangent line and a humidity ratio line, and (2) a second temperature defined by an intersection of a cold side tangent line and the humidity ratio line.

23. An apparatus for forming at least two air streams across a doorway between areas of relatively cool and warm air masses using first and second air curtains, each including a supply air plenum with an outlet aperture at one side of the doorway, a return air duct with an inlet aperture at another side of the doorway and an intermediate air duct extending between the supply plenum and return air duct, and an air mover for moving an air stream across the doorway into the air curtain's respective inlet aperture to the return air duct through the intermediate air duct to the supply air plenum and out of the outlet aperture, the apparatus comprising:

a heater in thermal communication with the air stream from at least one of the air curtains for warming the air stream of the particular air curtain;

a control unit controlling the operation of the heater;

a first air sensor located in one of the relatively cool and warm air areas providing an air characteristic input to the control unit; and a second air sensor located in contact with the air stream providing an air stream characteristic input to the control unit;

wherein the control unit continuously monitors the air characteristic input and the air stream characteristic input and operates the heater to maintain the temperature of the air stream at the greater of (1) a first temperature defined by an intersection of a warm side tangent line and a humidity ratio line, and (2) a second temperature defined by an intersection of a cold side tangent line and the humidity ratio line.

24. A method of maintaining a non-saturated air stream across a doorway between areas of relatively cool and warm air masses so as to prevent condensation and the formation fog or frost at the doorway, wherein the air stream is generated by an air curtain including a supply air plenum with an outlet aperture at a first side of the doorway through which an air stream is forced across the doorway to an inlet aperture of a return air duct at a second side of the doorway, the method comprising:

monitoring continuously the condition of the air stream and the condition of at least one of the relatively cool and warm ambient air areas; and conditioning the air stream to maintain the temperature and humidity of the air stream at the greater of (1) a first temperature defined by an intersection of a warm side tangent line and a humidity ratio line, and (2) a second temperature defined by an intersection of a cold side tangent line and the humidity ratio line.

25. A method of controlling air flow in an air curtain arrangement having a plurality of air curtains, the method comprising:

calculating a humidity ratio for the air curtain arrangement based upon an intersection of a warm side tangent line to a psychrometric saturating curve and a cold side tangent line to the curve;

adjusting relative volumetric air flow of the air curtains to maintain operation of the air curtain arrangement at the calculated humidity ratio; and maintaining a temperature of an air stream in at least one of the air curtains at the greater of (1) a first temperature defined by an intersection of a warm side tangent line and a humidity ratio line, and (2) a second temperature defined by an intersection of a cold side tangent line and the humidity ratio line.

26. The apparatus of claim 23, wherein the control unit controls relative volumetric airflow between at least two of the air streams to adjust a humidity ratio of the apparatus.

27. The method of claim 24, wherein the conditioning further comprises controlling relative volumetric airflow between at least two of the air streams to adjust a humidity ratio of the apparatus.

28. The air curtain arrangement of claim 1,
further comprising a second discharge means that discharges a second air stream across the doorway;
wherein the control unit controls relative volumetric airflow as between the air stream and the second air stream to maintain operation of the air curtain based on the humidity ratio.

\* \* \* \* \*